US012642569B2

(12) United States Patent
Croft et al.

(10) Patent No.: US 12,642,569 B2
(45) Date of Patent: Jun. 2, 2026

(54) ELECTROSURGICAL INSTRUMENTS INCLUDING THERMAL CUTTING ELEMENTS

(71) Applicant: Covidien LP, Mansfield, MA (US)

(72) Inventors: Richard L. Croft, Mead, CO (US); Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 357 days.

(21) Appl. No.: 18/025,106

(22) PCT Filed: Aug. 24, 2021

(86) PCT No.: PCT/US2021/047291
§ 371 (c)(1),
(2) Date: Mar. 7, 2023

(87) PCT Pub. No.: WO2022/066337
PCT Pub. Date: Mar. 31, 2022

(65) Prior Publication Data
US 2023/0329768 A1     Oct. 19, 2023

Related U.S. Application Data

(60) Provisional application No. 63/081,393, filed on Sep. 22, 2020.

(51) Int. Cl.
*A61B 18/12* (2006.01)
*A61B 18/08* (2006.01)
(Continued)

(52) U.S. Cl.
CPC ........ *A61B 18/085* (2013.01); *A61B 18/1445* (2013.01); *A61B 2018/00607* (2013.01);
(Continued)

(58) Field of Classification Search
CPC .... A61B 18/085; A61B 18/1442–1447; A61B 2018/145–146
See application file for complete search history.

(56) References Cited

U.S. PATENT DOCUMENTS

| | | | |
|---|---|---|---|
| 4,196,734 A | 4/1980 | Harris | |
| 4,493,320 A | 1/1985 | Treat | |

(Continued)

FOREIGN PATENT DOCUMENTS

| | | | |
|---|---|---|---|
| WO | 2020154100 A1 | 7/2020 | |

OTHER PUBLICATIONS

International Search Report and Written Opinion issued in correponding International Application No. PCT/US2021/047291 mailed Dec. 22, 2021, 9 pages.

*Primary Examiner* — Daniel W Fowler

(57) ABSTRACT

A surgical system includes an end effector assembly having first and second jaw members configured to grasp tissue between tissue contacting surfaces thereof. An electromagnetic induction coil is fixedly disposed within the second jaw member. A thermal cutting element is disposed at least partially within the electromagnetic induction coil and movable relative to the electromagnetic induction coil and the second jaw member between a retracted position, wherein the thermal cutting element is flush with or recessed within the second jaw member, and an extended position, wherein the thermal cutting element protrudes from the second jaw member. The thermal cutting element is formed at least partially from an electromagnetic material capable of being inductively heated. The electromagnetic induction coil is adapted to connect to a source of energy to produce an electromagnetic field within the electromagnetic induction coil to thereby inductively heat the thermal cutting element.

17 Claims, 11 Drawing Sheets

(51) Int. Cl.
    *A61B 18/14*          (2006.01)
    *A61B 18/00*          (2006.01)
(52) U.S. Cl.
    CPC .............. *A61B 2018/00791* (2013.01); *A61B*
                                    *2018/1455* (2013.01)

(56)                References Cited

U.S. PATENT DOCUMENTS

| | | |
|---|---|---|
| 4,701,587 A | 10/1987 | Carter et al. |
| 4,752,673 A | 6/1988 | Krumme |
| 4,807,620 A | 2/1989 | Strul et al. |
| 4,848,337 A | 7/1989 | Shaw et al. |
| 4,860,745 A | 8/1989 | Farin et al. |
| 4,877,944 A | 10/1989 | Cowell et al. |
| 4,905,691 A | 3/1990 | Rydell |
| 4,914,267 A | 4/1990 | Derbyshire |
| 4,938,761 A | 7/1990 | Ensslin |
| 5,003,991 A | 4/1991 | Takayama et al. |
| 5,047,025 A | 9/1991 | Taylor et al. |
| 5,087,804 A | 2/1992 | McGaffigan |
| 5,182,427 A | 1/1993 | McGaffigan |
| 5,189,271 A | 2/1993 | Derbyshire |
| 5,250,046 A | 10/1993 | Lee |
| 5,300,068 A | 4/1994 | Rosar et al. |
| 5,300,750 A | 4/1994 | Carter, Jr. et al. |
| 5,308,311 A | 5/1994 | Eggers et al. |
| 5,540,679 A | 7/1996 | Fram et al. |
| 5,628,771 A | 5/1997 | Mizukawa et al. |
| 5,707,369 A | 1/1998 | Vaitekunas et al. |
| 5,707,402 A | 1/1998 | Heim |
| 5,807,392 A | 9/1998 | Eggers |
| 5,827,271 A | 10/1998 | Buysse et al. |
| 5,876,401 A | 3/1999 | Schulze et al. |
| 5,911,719 A | 6/1999 | Eggers |
| 6,086,586 A | 7/2000 | Hooven |
| 6,221,039 B1 | 4/2001 | Durgin et al. |
| 6,235,027 B1 | 5/2001 | Herzon |
| 6,273,887 B1 | 8/2001 | Yamauchi et al. |
| 6,602,252 B2 | 8/2003 | Mollenauer |
| 6,626,901 B1 | 9/2003 | Treat et al. |
| 6,692,489 B1 | 2/2004 | Heim et al. |
| 6,726,683 B1 | 4/2004 | Shaw |
| 6,736,813 B2 | 5/2004 | Yamauchi et al. |
| 6,776,780 B2 | 8/2004 | Mulier et al. |
| 6,802,843 B2 | 10/2004 | Truckai et al. |
| 6,808,525 B2 | 10/2004 | Latterell et al. |
| 6,860,880 B2 | 3/2005 | Treat et al. |
| 6,929,641 B2 | 8/2005 | Goble et al. |
| 7,011,656 B2 | 3/2006 | McGaffigan et al. |
| 7,025,065 B2 | 4/2006 | McGaffigan et al. |
| 7,033,356 B2 | 4/2006 | Latterell et al. |
| 7,070,597 B2 | 7/2006 | Truckai et al. |
| 7,083,619 B2 | 8/2006 | Truckai et al. |
| 7,112,201 B2 | 9/2006 | Truckai et al. |
| 7,125,409 B2 | 10/2006 | Truckai et al. |
| 7,147,637 B2 | 12/2006 | Goble |
| 7,169,146 B2 | 1/2007 | Truckai et al. |
| 7,204,835 B2 | 4/2007 | Latterell et al. |
| 7,211,079 B2 | 5/2007 | Treat |
| 7,270,664 B2 | 9/2007 | Johnson et al. |
| 7,276,068 B2 | 10/2007 | Johnson et al. |
| 7,326,202 B2 | 2/2008 | McGaffigan |
| 7,329,255 B2 | 2/2008 | McGaffigan |
| 7,354,440 B2 | 4/2008 | Truckal et al. |
| 7,357,802 B2 | 4/2008 | Palanker et al. |
| 7,815,641 B2 | 10/2010 | Dodde et al. |
| 7,931,649 B2 | 4/2011 | Couture et al. |
| 7,972,334 B2 | 7/2011 | McGreevy et al. |
| 8,034,051 B2 | 10/2011 | Martin et al. |
| 8,187,273 B2 | 5/2012 | Kerr et al. |
| 8,197,472 B2 | 6/2012 | Lau et al. |

| | | |
|---|---|---|
| 8,292,879 B2 | 10/2012 | Manwaring et al. |
| 8,382,748 B2 | 2/2013 | Geisel |
| 8,394,094 B2 | 3/2013 | Edwards et al. |
| 8,480,666 B2 | 7/2013 | Buysse et al. |
| 8,491,626 B2 | 7/2013 | Roy et al. |
| 8,551,088 B2 | 10/2013 | Falkenstein et al. |
| 8,597,297 B2 | 12/2013 | Couture et al. |
| 8,617,151 B2 | 12/2013 | Denis et al. |
| 8,623,003 B2 | 1/2014 | Lau et al. |
| 8,734,445 B2 | 5/2014 | Johnson et al. |
| 8,915,909 B2 | 12/2014 | Manwaring et al. |
| 8,932,279 B2 | 1/2015 | Stringham et al. |
| 8,951,248 B2 | 2/2015 | Messerly et al. |
| 9,005,199 B2 | 4/2015 | Beckman et al. |
| 9,039,694 B2 | 5/2015 | Ross et al. |
| 9,050,100 B2 | 6/2015 | Yates et al. |
| 9,084,606 B2 | 7/2015 | Greep |
| 9,131,977 B2 | 9/2015 | Manwaring et al. |
| 9,192,427 B2 | 11/2015 | Johnson et al. |
| 9,265,556 B2 | 2/2016 | Manwaring et al. |
| 9,387,037 B2 | 7/2016 | Yang |
| 9,402,679 B2 | 8/2016 | Ginnebaugh et al. |
| 9,918,774 B2 | 3/2018 | Batchelor et al. |
| 9,931,157 B2 | 4/2018 | Strobl et al. |
| 9,955,858 B2 | 5/2018 | Pamnani et al. |
| 10,204,773 B2 | 2/2019 | Sugiyama et al. |
| 10,213,247 B2 | 2/2019 | Manwaring et al. |
| 2003/0040744 A1 | 2/2003 | Latterell et al. |
| 2003/0130658 A1 | 7/2003 | Goble et al. |
| 2003/0144660 A1 | 7/2003 | Mollenauer |
| 2003/0171747 A1 | 9/2003 | Kanehira et al. |
| 2004/0030330 A1 | 2/2004 | Brassell et al. |
| 2004/0049185 A1 | 3/2004 | Latterell et al. |
| 2004/0167506 A1 | 8/2004 | Chen |
| 2004/0176756 A1 | 9/2004 | McGaffigan |
| 2005/0107776 A1 | 5/2005 | McGaffigan et al. |
| 2006/0212030 A1 | 9/2006 | McGaffigan |
| 2006/0217706 A1 | 9/2006 | Lau et al. |
| 2007/0074807 A1 | 4/2007 | Guerra |
| 2007/0156137 A1 | 7/2007 | Geisel |
| 2007/0270924 A1 | 11/2007 | McCann et al. |
| 2009/0248002 A1 | 10/2009 | Takashino et al. |
| 2010/0152725 A1 | 6/2010 | Pearson et al. |
| 2010/0198216 A1 | 8/2010 | Palanker |
| 2010/0268211 A1 | 10/2010 | Manwaring et al. |
| 2011/0054455 A1* | 3/2011 | Lee ..................... A61B 18/082 |
| | | 606/28 |
| 2011/0077629 A1 | 3/2011 | Tanaka et al. |
| 2011/0270250 A1 | 11/2011 | Horner et al. |
| 2012/0226270 A1 | 9/2012 | Manwaring et al. |
| 2012/0330295 A1 | 12/2012 | Manwaring et al. |
| 2013/0012934 A1 | 1/2013 | Manwaring et al. |
| 2013/0018411 A1 | 1/2013 | Collings et al. |
| 2013/0046303 A1 | 2/2013 | Evans et al. |
| 2013/0046337 A1 | 2/2013 | Evans et al. |
| 2013/0066310 A1* | 3/2013 | Manwaring ............ A61B 18/10 |
| | | 606/29 |
| 2013/0123837 A1 | 5/2013 | Roy et al. |
| 2014/0100600 A1* | 4/2014 | Kendrick ........... A61B 17/2841 |
| | | 606/205 |
| 2014/0135804 A1 | 5/2014 | Weisenburgh, II et al. |
| 2014/0194875 A1 | 7/2014 | Reschke et al. |
| 2014/0276796 A1 | 9/2014 | Batchelor et al. |
| 2015/0018825 A1 | 1/2015 | Takashino |
| 2015/0032094 A1 | 1/2015 | Kane et al. |
| 2015/0051598 A1 | 2/2015 | Orszulak et al. |
| 2015/0320485 A1 | 11/2015 | Batchelor et al. |
| 2016/0249971 A1 | 9/2016 | Manwaring et al. |
| 2017/0196648 A1 | 7/2017 | Ward et al. |
| 2017/0348042 A1 | 12/2017 | Drochner et al. |
| 2019/0000538 A1 | 1/2019 | Widenhouse et al. |
| 2020/0237423 A1* | 7/2020 | Witte ................. A61G 13/1245 |

* cited by examiner

ELECTROSURGICAL INSTRUMENTS INCLUDING THERMAL CUTTING ELEMENTS

CROSS-REFERENCE TO RELATED APPLICATIONS

This application is a 371 National Stage Application of International Application No. PCT/US2021/047291, filed Aug. 24, 2021, which claims benefit of U.S. Provisional Patent Application No. 63/081,393, filed Sep. 22, 2020, the entire contents of each of which is hereby incorporated herein by reference.

FIELD

The present disclosure relates to electrosurgical instruments and, more particularly, to electrosurgical instruments including thermal cutting elements to facilitate tissue treatment, e.g., sealing and cutting of tissue.

BACKGROUND

A surgical forceps is a pliers like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, energy-based tissue cutting may be employed to cut the treated tissue using energy, e.g., thermal, electrosurgical, ultrasonic, light, or other suitable energy.

SUMMARY

As used herein, the term "distal" refers to the portion that is being described which is farther from an operator (whether a human surgeon or a surgical robotic), while the term "proximal" refers to the portion that is being described which is closer to the operator. Terms including "generally," "about," "substantially," and the like, as utilized herein, are meant to encompass variations up to and including plus or minus 10 percent to take into account, for example, material, measurement, manufacturing, environmental, use, and/or other tolerances and variations. Further, to the extent consistent, any or all of the aspects detailed herein may be used in conjunction with any or all of the other aspects detailed herein.

Provided in accordance with aspects of the present disclosure is a surgical system including an end effector assembly having first and second jaw members each including a tissue contacting surface. At least one of the first or second jaw members is movable relative to the other between a spaced apart position and an approximated position for grasping tissue between the tissue contacting surfaces. An electromagnetic induction coil is fixedly disposed within the second jaw member. A thermal cutting element is disposed at least partially within the electromagnetic induction coil and movable relative to the electromagnetic induction coil and the second jaw member between a retracted position, wherein the thermal cutting element is flush with or recessed within the second jaw member, and an extended position, wherein the thermal cutting element protrudes from the second jaw member. The thermal cutting element is formed at least partially from an electromagnetic material capable of being inductively heated. The electromagnetic induction coil is adapted to connect to a source of energy to produce an electromagnetic field within the electromagnetic induction coil to thereby inductively heat the thermal cutting element.

In an aspect of the present disclosure, the tissue contacting surfaces are formed from an electrically-conductive material and adapted to connect to a source of energy for electrosurgically treating tissue grasped between the tissue contacting surfaces.

In another aspect of the present disclosure, the tissue contacting surface of the second jaw member defines a channel therethrough. In the extended position, the thermal cutting element protrudes through the channel to extend from the tissue contacting surface of the second jaw member.

In yet another aspect of the present disclosure, the thermal cutting element is biased towards the retracted position or the extended position.

In still another aspect of the present disclosure, a deployment mechanism is provided for selectively moving the thermal cutting element from the retracted position to the extended position.

In still yet another aspect of the present disclosure, the deployment mechanism includes a threaded drive shaft including a cam block threadingly engaged thereon. Rotation of the threaded drive shaft translates the cam block to interact with a cam surface associated with the thermal cutting element to move the thermal cutting element towards the extended position.

In another aspect of the present disclosure, the deployment mechanism includes a drive shaft including a cam block engaged therewith. Translation of the drive shaft translates the cam block to interact with a cam surface associated with the thermal cutting element to move the thermal cutting element towards the extended position.

In yet another aspect of the present disclosure, the deployment mechanism includes a drive shaft including a cam roller rotatably engaged therewith. Translation of the drive shaft translates the cam roller to roll along a cam surface associated with the thermal cutting element to move the thermal cutting element towards the extended position.

In another aspect of the present disclosure, the deployment mechanism includes a drive shaft having a cam lobe engaged therewith in an offset position. Rotation of the drive shaft rotates the cam lobe to interact with a cam surface associated with the thermal cutting element to move the thermal cutting element towards the extended position.

In still another aspect of the present disclosure, deployment of the thermal cutting element and heating of the thermal cutting element are independently initiated. Alternatively, deployment of the thermal cutting element and heating of the thermal cutting element are at least partly dependent upon one another.

In yet another aspect of the present disclosure, deployment and/or retraction of the thermal cutting element is inhibited based on a temperature of the thermal cutting element.

In still yet another aspect of the present disclosure, heating of the thermal cutting element is inhibited based on a position of the thermal cutting element.

In another aspect of the present disclosure, the thermal cutting element is formed at least partially from a ferromagnetic material.

In another aspect of the present disclosure, the thermal cutting element is configured to be heated to or near a Curie point temperature of the material forming the thermal cutting element. The temperature of the thermal cutting element may be controlled via automatic Curie point temperature control, e.g., via the Curie effect, where a ferromagnetic material becomes paramagnetic at its Curie temperature and heating due to magnetic induction is significantly reduced affording a temperature control effect.

In yet another aspect of the present disclosure, the surgical system further includes an LC circuit configured to enable temperature-based control of heating of the thermal cutting element based on a relationship between oscillation frequency of the LC circuit and temperature of the thermal cutting element.

In still another aspect of the present disclosure, the surgical system further includes a generator configured to monitor inductance or resistance of the thermal cutting element and to enable temperature-based control of heating of the thermal cutting element based on a relationship between inductance or resistance of the thermal cutting element and temperature of the thermal cutting element.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1A:
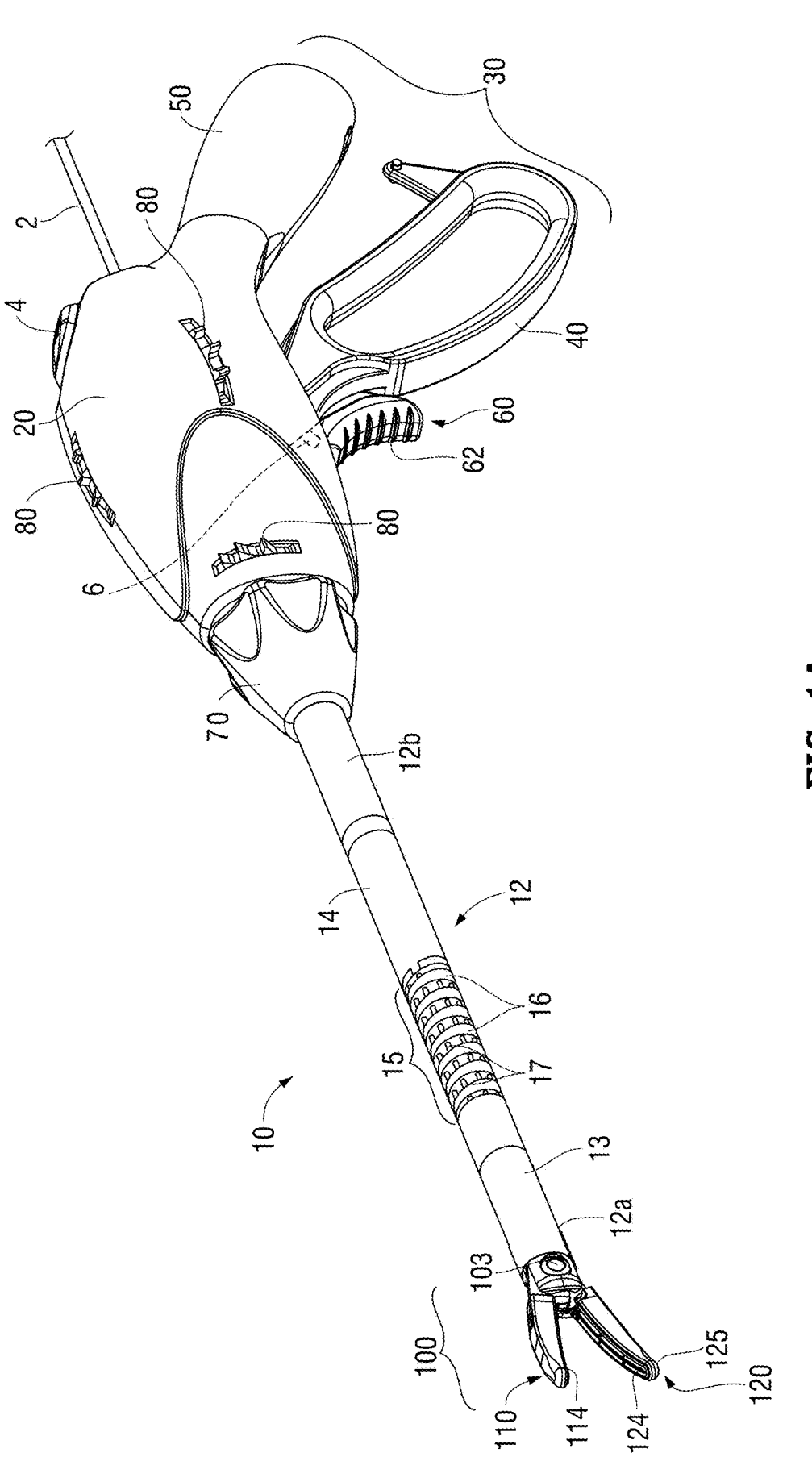
FIG. 1A is a perspective view of a shaft-based electrosurgical forceps provided in accordance with the present disclosure wherein a shaft of the forceps is disposed in a non-articulated position and wherein jaw members of an end effector assembly of the forceps are disposed in a spaced apart position.
Figure 1B:
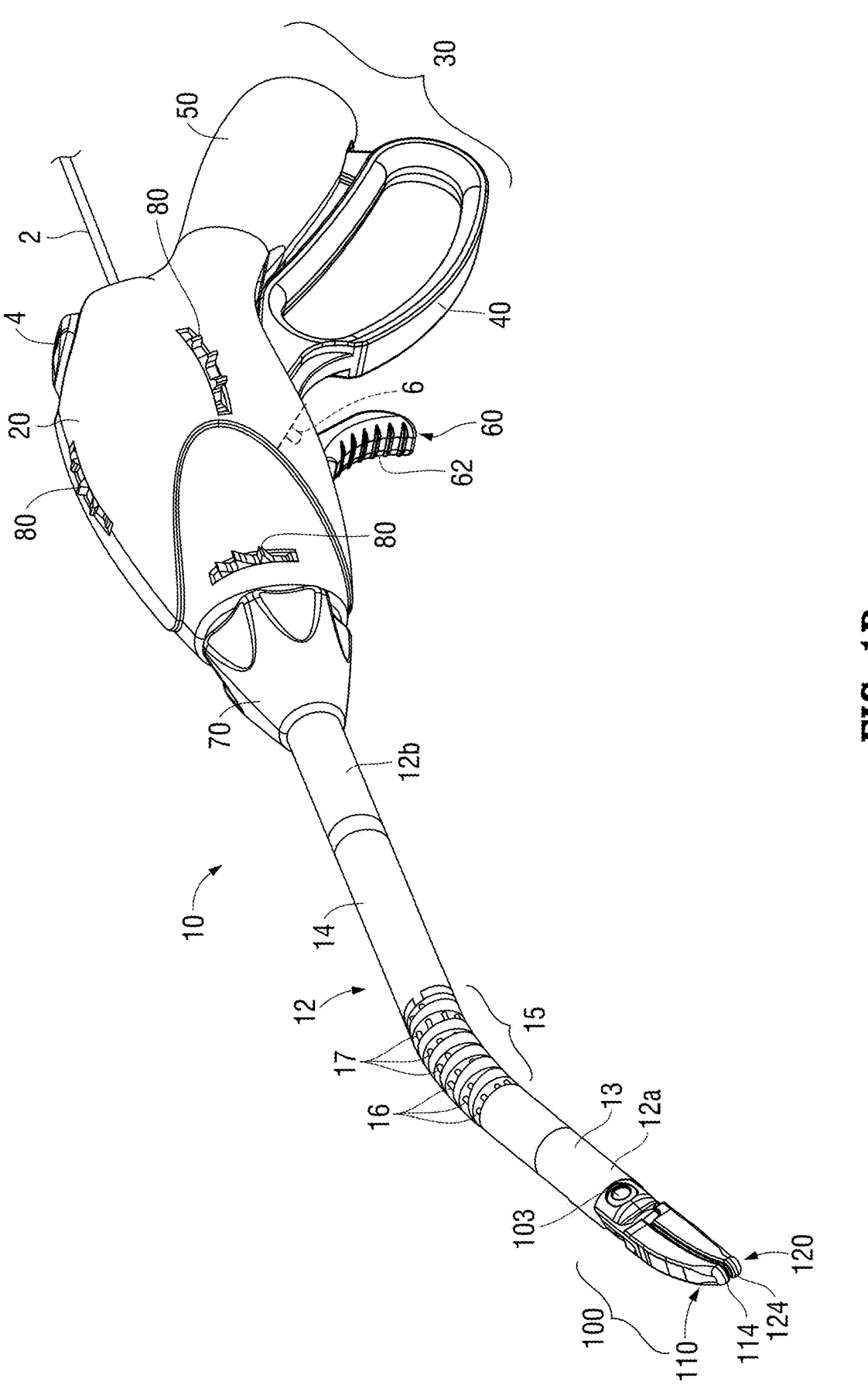
FIG. 1B is a perspective view of the forceps of FIG. 1A, wherein the shaft of the forceps is disposed in an articulated position and wherein the jaw members of the forceps are disposed in an approximated position.

Turning to FIGS. 1A and 1B, a shaft based electrosurgical forceps provided in accordance with the present disclosure is shown generally identified by reference numeral 10. For the purposes herein, forceps 10 is generally described.

Aspects and features of surgical forceps 10 not germane to the understanding of the present disclosure are omitted to avoid obscuring the aspects and features of the present disclosure in unnecessary detail.

Figure 4:
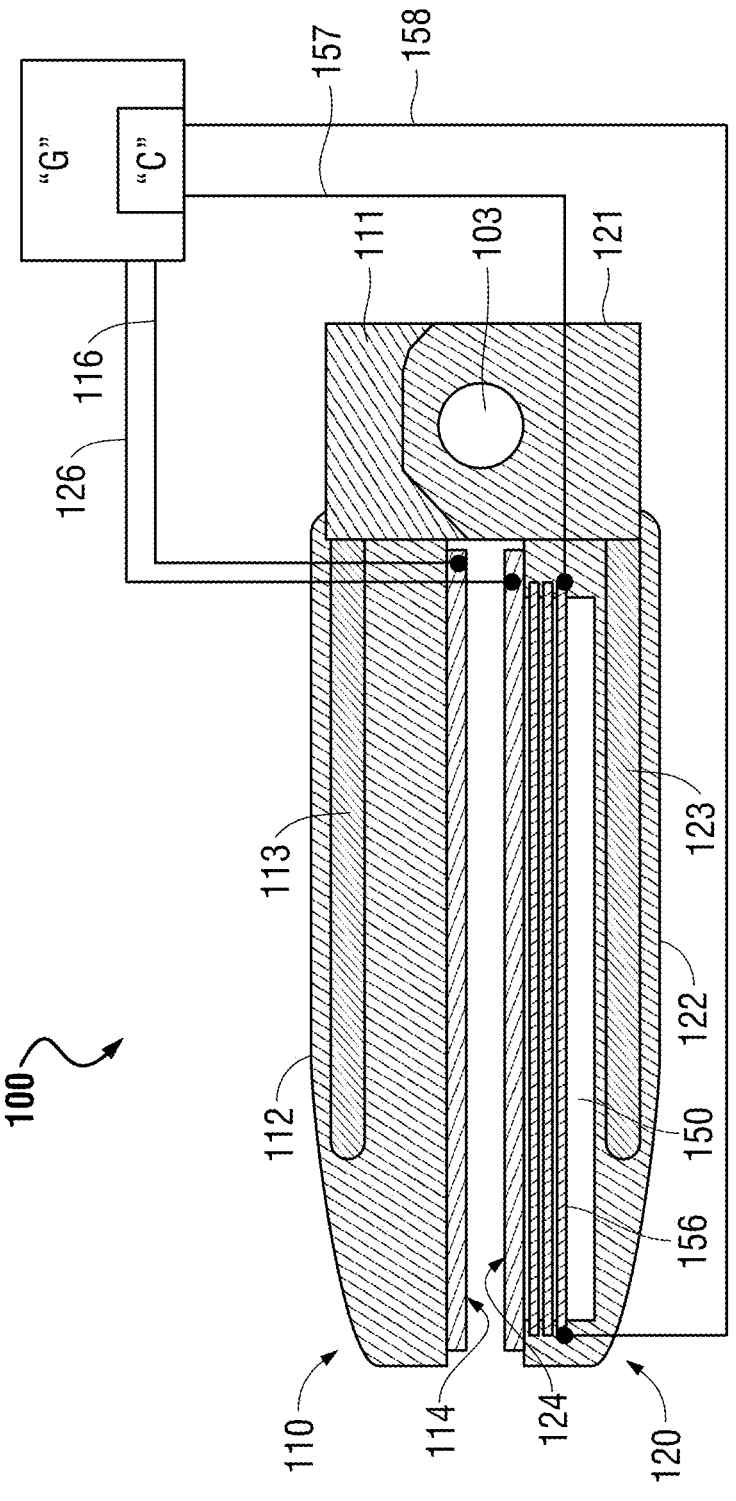
FIG. 4 is a longitudinal, cross-sectional view of the end effector assembly of the forceps of FIG. 1A, configured for use with the hemostat-style electrosurgical forceps of FIG. 2, configured for use the robotic surgical system of FIG. 3, or configured for use with any other suitable surgical instrument or system, wherein a thermal cutting element thereof is disposed in a retracted position.
Figure 5:
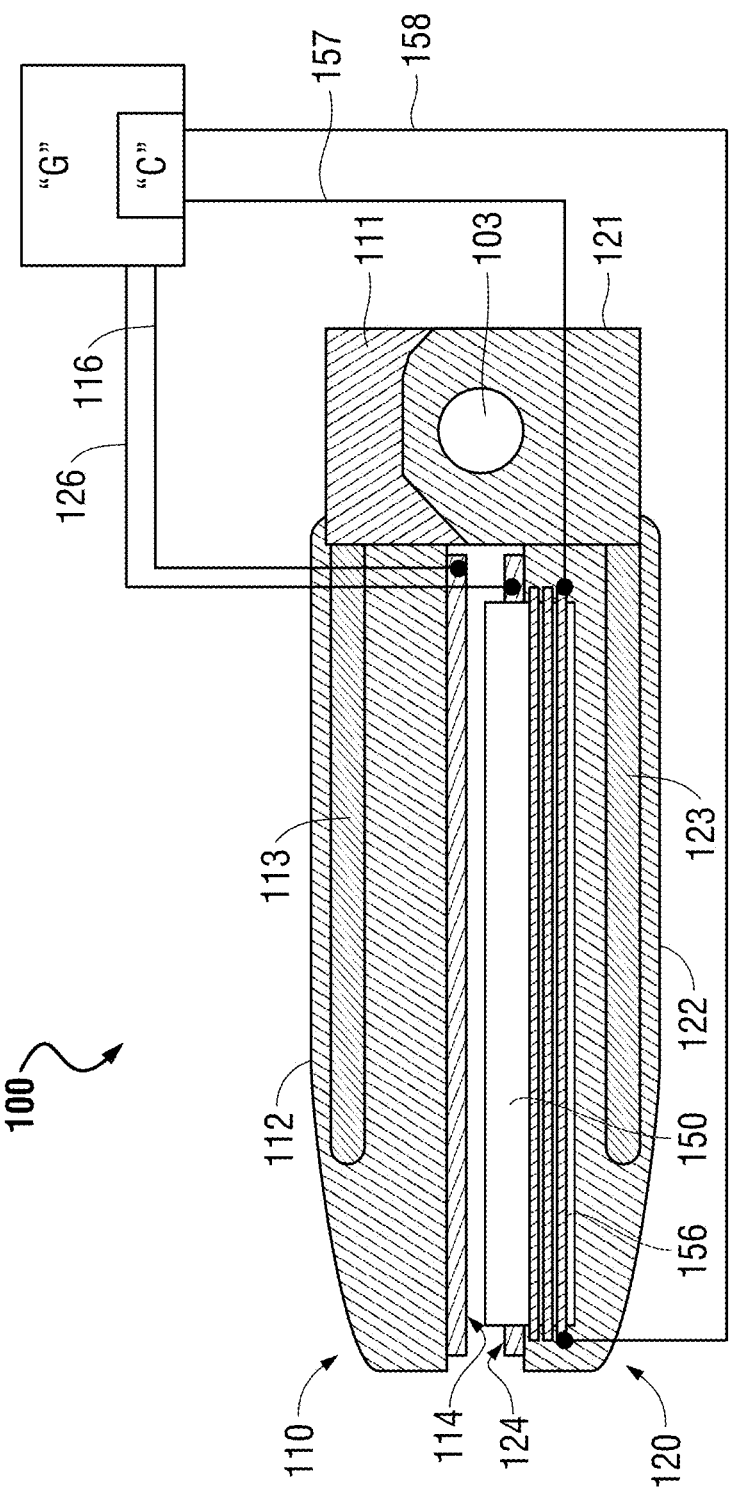
FIG. 5 is a longitudinal, cross-sectional view of the end effector assembly of FIG. 4, wherein the thermal cutting element is disposed in an extended position.

Forceps 10 includes a housing 20, a handle assembly 30, a trigger assembly 60, a rotating assembly 70, a plurality of articulation actuators 80, one or more activation switches 4, 6, and an end effector assembly 100. Forceps 10 further includes a shaft 12 having a distal end portion 12a configured to mechanically engage end effector assembly 100 and a proximal end portion 12b that mechanically engages housing 20. Forceps 10 also includes cable 2 that connects forceps 10 to an energy source, e.g., a generator "G" (FIGS. 4 and 5) or other suitable energy source, although forceps 10 may alternatively be configured as a battery-powered device including an on-board generator. Cable 2 includes a plurality of wires (not shown) extending therethrough that have sufficient length to extend into housing 20 and through shaft 12 in order to provide energy to one or both tissue contacting surfaces 114, 124 of jaw members 110, 120, respectively, of end effector assembly 100 to enable electrosurgical tissue treatment, e.g., sealing, cauterizing, coagulating/desiccating, etc., of tissue grasped between tissue contacting surfaces 114, 124. Similar or different wires (not shown) of cable 2 extend into housing 20 and through shaft 12 in order to enable energization of thermal cutting element 150 (FIGS. 4 and 5) of end effector assembly 100 for thermally treating, e.g., cutting, spot cauterizing or coagulating, etc., tissue in contact with thermal cutting element 150 (FIGS. 4 and 5). Similar or different wires (not shown) also electrically couple the one or more activation switches 4, 6 of forceps 10 to tissue contacting surfaces 114, 124, thermal cutting element 150 (FIGS. 4 and 5), and/or the source of energy, e.g., generator "G" (FIGS. 4 and 5), to enable selective initiation of electrosurgical tissue treatment and/or thermal tissue treatment.

In some configurations, a single activated position activation switch 4 may be provided to automatically initiate electrosurgical tissue treatment (e.g., tissue sealing) and thermal tissue treatment (e.g., tissue cutting) upon activation, e.g., to first initiate sealing and, once sealing is complete, initiate cutting. Suitable feedback, sensors, or other suitable mechanism(s) to determine seal completion and to initiate cutting when seal completion is determined may be utilized. Alternatively, suitable feedback, sensors, or other suitable mechanism(s) may be utilized to determine instrument state (e.g., jaws open, jaws closed, thermal cutting element retracted, thermal cutting element deployed, etc.), tissue presence, a position/type/thickness of tissue, whether the end effector assembly is stationary or moving, whether sealing has been completed, etc., and, based thereon, automatically initiate or deactivate sealing or cutting. Further still, activation switch 4 may be a multi-activated position switch wherein each position corresponds to a different mode of operation, e.g., a first position for sealing and a second activation position for cutting. In yet other configurations, multiple different activation switches 4, 6 may be provided, e.g., one for initiating sealing and another for initiating cutting.

Shaft 12 of forceps 10 defines a distal segment 13 positioned towards distal end portion 12a thereof, a proximal segment 14 positioned towards proximal end portion 12b thereof, and an articulating section 15 disposed between the distal and proximal segments 13, 14, respectively. Articulating section 15 includes at least one articulating link 16 having a plurality of articulation cables 17 extending therethrough. Each cable 17 is operably engaged at its distal end to distal segment 13 and at its proximal end to one of the articulation actuators 80 so as to enable articulation of distal segment 13 and, thus, end effector assembly 100, relative to proximal segment 14 upon actuation of one or more of articulation actuators 80. In some aspects, articulating section 15 and articulation actuators 80 are omitted such that shaft 12 of forceps 10 does not articulate. In either configuration, rotating assembly 70 operably couples shaft 12 to housing 20 so as to enable selective rotation of shaft 12 and, thus, end effector assembly 100, relative to housing 20.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced apart position (FIG. 1A) and an approximated position (FIG. 1B) to grasp tissue between tissue contacting surfaces 114, 124 of jaw members 110, 120, respectively. As shown in FIG. 1A, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120 (FIG. 1B).

Trigger assembly 60 includes a trigger 62 coupled to housing 20 and movable relative thereto between an un-actuated position and an actuated position. Trigger 62 is operably coupled to a deployment mechanism, various configurations of which are detailed below, so as to enable selective deployment of thermal cutting element 150 (FIGS. 4 and 5) from a retracted position (FIG. 4), wherein thermal cutting element 150 (FIGS. 4 and 5) is flushed with or recessed within jaw member 120 (see FIG. 4), to an extended position (FIG. 5), wherein thermal cutting element 150 (FIGS. 4 and 5) protrudes upwardly from tissue contacting surface 124 of jaw member 120 (see FIG. 5), e.g., through a channel 125 defined within tissue contacting surface 124, to enable thermal cutting of tissue. As an alternative to a pivoting trigger 62, a slide trigger, push-button, toggle switch, or other suitable actuator may be provided. Further, in aspects where multiple activation switches 4, 6 are provided, the switch, e.g., switch 6, associated with initiating thermal cutting may be positioned in the actuation path of trigger 62 such that, initially upon movement of trigger 62 from the un-actuated position, upon completion of movement of trigger 62 from the un-actuated position to the actuated position, or at any suitable point along the actuation path of trigger 62 from the un-actuated position to the actuated position, switch 6 is activated to initiate thermal cutting. Switch 6 may be similarly be deactivated upon return of trigger 62 to the un-actuated position.

End effector assembly 100, as noted above, includes first and second jaw members 110, 120 pivotably coupled to one another about pivot 103 for moving one or both of jaw members 110, 120 relative to the other between the spaced-apart and approximated positions. Each jaw member 110, 120 includes a tissue contacting surfaces 114, 124, respectively, thereon, and one or both of the jaw members 110, 120, e.g., jaw member 120, includes a thermal cutting element 150 (FIGS. 4 and 5) selectively deployable therefrom to enable thermal cutting of tissue. Jaw members 110, 120 may define curved configurations wherein each jaw member is similarly curved laterally off of a longitudinal axis of end effector assembly 100. However, other suitable curved configurations including curvature towards one of the jaw members 110, 120 (and thus away from the other), multiple curves with the same plane, and/or multiple curves within different planes are also contemplated. Alternatively, jaw members 110, 120 may define straight or angled configurations. End effector assembly 100 is described in greater detail below with reference to FIGS. 4 and 5.

Figure 2:
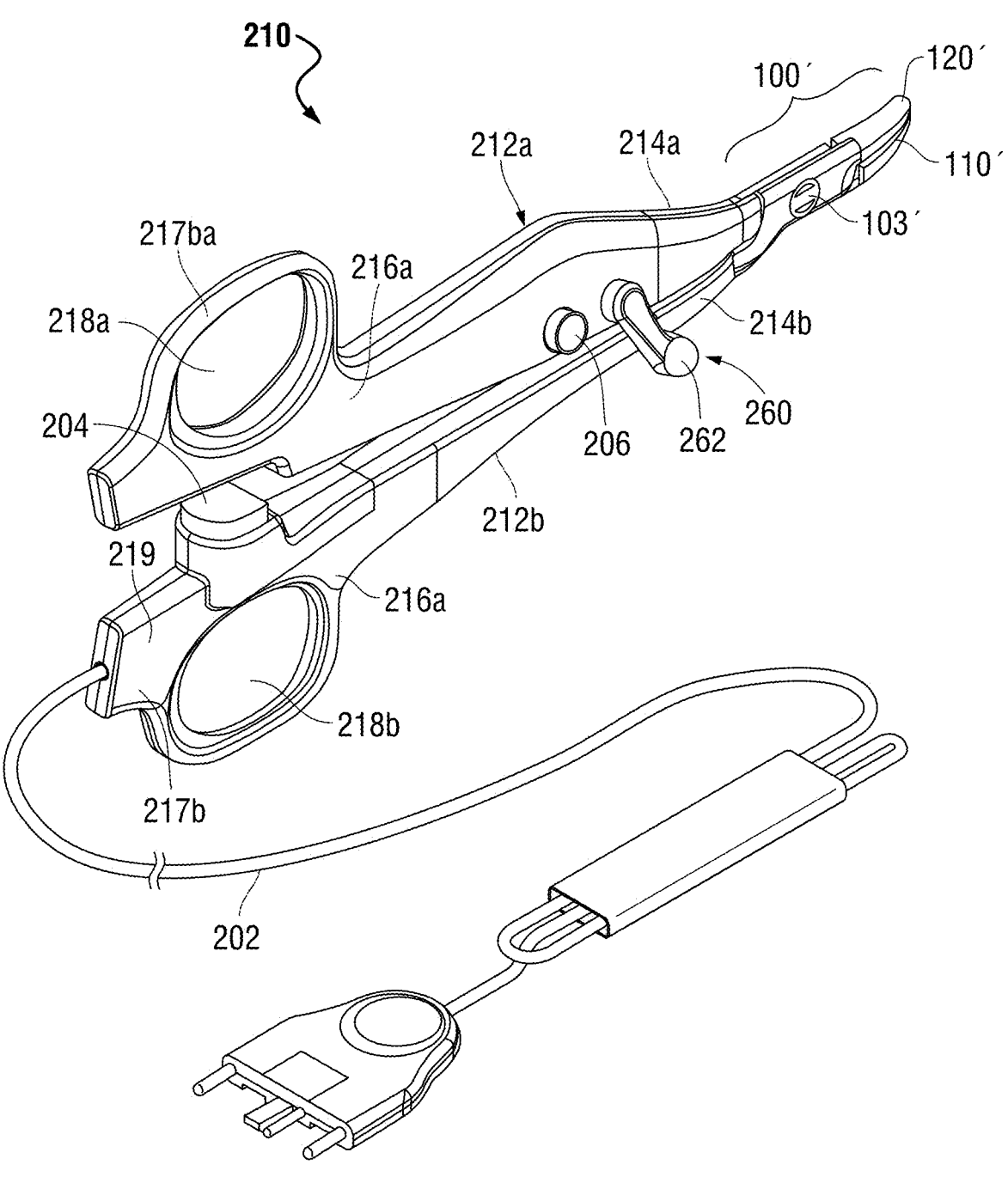
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. For the purposes herein, surgical forceps 210 is generally described. Aspects and features of open surgical forceps 210 not germane to the understanding of the present disclosure are omitted to avoid obscuring the aspects and features of the present disclosure in unnecessary detail.

Forceps 210 includes two elongated shafts 212a, 212b, each having a proximal end portion 216a, 216b, and a distal end portion 214a, 214b, respectively. Forceps 210 is configured for use with an end effector assembly 100' similar to and including any of the features of end effector assembly 100 (FIGS. 1A, 1B, 4, and 5). More specifically, end effector assembly 100' includes first and second jaw members 110', 120' attached to respective distal end portions 214a, 214b of shafts 212a, 212b and movable about a pivot 103' to grasp, treat, e.g., seal, and/or thermally cut tissue. Each shaft 212a, 212b includes a handle 217a, 217b disposed at the proximal end portion 216a, 216b thereof. Each handle 217a, 217b defines a finger hole 218a, 218b therethrough for receiving a finger of the user. As can be appreciated, finger holes 218a, 218b facilitate movement of the shafts 212a, 212b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shafts 212a, 212b of forceps 210, e.g., shaft 212b, includes a proximal shaft connector 219 configured to connect forceps 210 to a source of energy, e.g., generator "G" (FIGS. 4 and 5) or other suitable energy source. Proximal shaft connector 219 secures a cable 202 to forceps 210 such that the user may selectively supply energy to jaw members 110', 120' for treating tissue and for energy-based tissue cutting. More specifically, one or more activation switches 204, 206 are provided for supplying energy to jaw members 110', 120' to electrosurgically treat, e.g., seal, tissue and/or to a thermal cutting element (not shown, see thermal cutting element 150 (FIGS. 4 and 5)) of end effector assembly 100' to thermally treat, e.g., cut, tissue. Activation switch 204 may be positioned to be activated upon sufficient approximation of shaft members 212a, 212b to initiate electrosurgical treatment, while activation switch 206 may be activated during initiation, completion, or other portion of actuation of trigger 262 to initiate thermal treatment. Other suitable configurations of one or more activation switches 204, 206 such as those detailed above with respect to activation switches 4, 6 (FIGS. 1A and 1B) are also contemplated.

Forceps 210 further includes a trigger assembly 260 including a trigger 262 coupled to one of the shafts, e.g., shaft 212a, and movable relative thereto between an un-actuated position and an actuated position. Trigger 262 is operably coupled to a deployment mechanism, various configurations of which are detailed below, so as to enable selective deployment of a thermal cutting element (not shown, see thermal cutting element 150 (FIGS. 4 and 5)) between the tissue contacting surfaces of jaw members 110', 120' to thermally cut tissue grasped between jaw members 110,' 120'. Similarly as above, as an alternative to a pivoting trigger 262, a slide trigger, push-button, toggle switch, or other suitable actuator may be provided.

Figure 3:
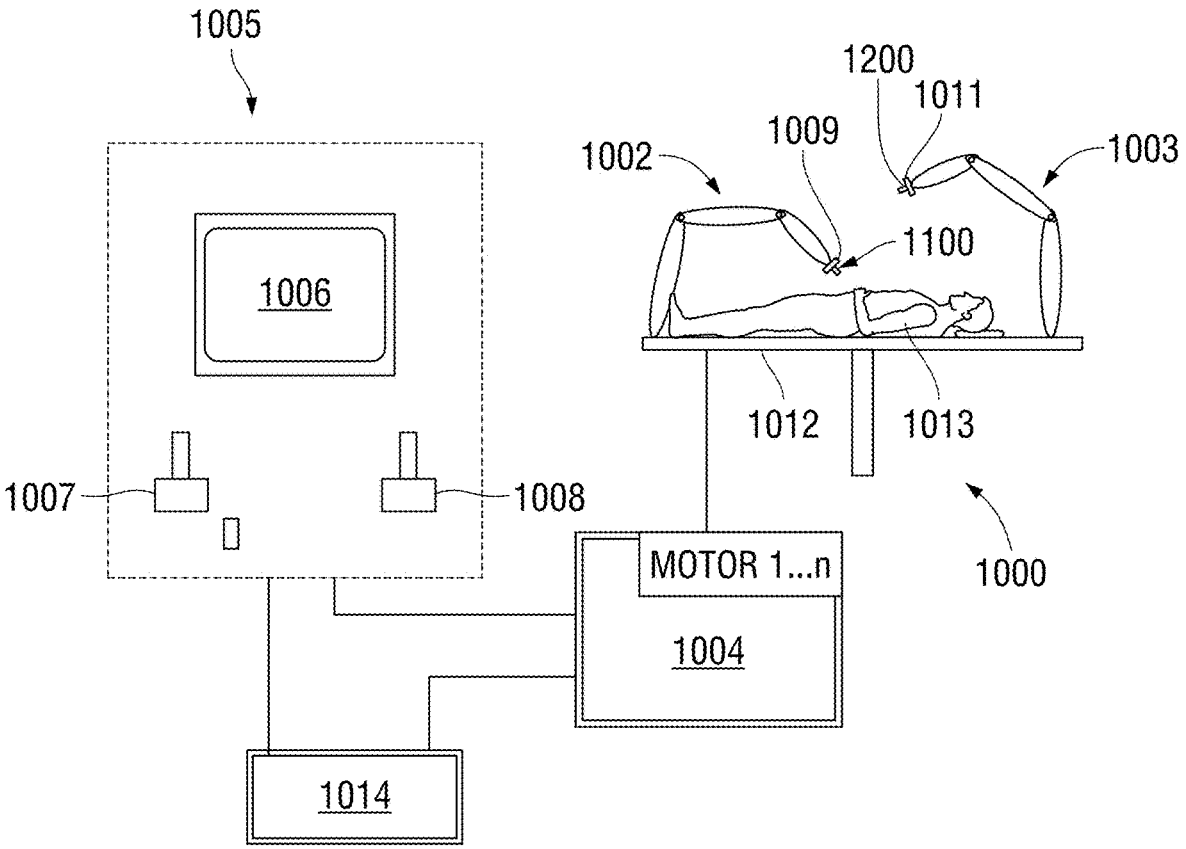
FIG. 3 is a schematic illustration of a robotic surgical system provided in accordance with the present disclosure.

Referring generally to FIG. 3, a robotic surgical system provided in accordance with the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include one or more sections, which are connected through joints, and an attaching device 1009, 1011, to which may be attached, for example, an end effector assembly 1100, 1200, respectively. End effector assembly 1100 may be similar to and include any of the features of end effector assembly 100 (FIGS. 1A, 1B, 4, and 5), although other suitable end effector assemblies for coupling to attaching device 1009 are also contemplated. End effector assembly 1200 may be any suitable end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Referring to FIGS. 4 and 5, end effector assembly 100 of shaft-based electrosurgical forceps 10 (FIGS. 1A and 1B) is described in more detail, although end effector assembly 100 may equally be applicable for use with hemostat-style electrosurgical forceps 210 (FIG. 2), robotic surgical system 1000 (FIG. 3), or any other suitable surgical instrument or system.

End effector assembly 100, as noted above, includes first and second jaw members 110, 120. Each jaw member 110, 120 includes a proximal flag portion 111, 121, an outer insulative jaw housing 112, 122, a structural body 113, 123, and a tissue contacting surface 114, 124, respectively. Proximal flag portions 111, 121 are pivotably coupled to one another about a pivot 103 to enable movement of one or both of jaw members 110, 120 relative to the other between the spaced-apart and approximated positions. Any suitable mechanism for pivoting jaw members 110, 120 relative to one another about pivot 103 may be utilized. Structural bodies 113, 123 may be formed with proximal flag portions 111, 121 or separate therefrom and, in either configuration, extend distally from proximal flag portions 111, 121 to support jaw housings 112, 122 and tissue contacting surfaces 114, 124, respectively, thereon.

Tissue contacting surfaces 114, 124 are connected to generator "G," e.g., via leads 116, 126, and are formed from electrically conductive material(s) to enable electrosurgical treatment of tissue grasped therebetween. For example, generator "G" may be configured to energize tissue contacting surfaces 114, 124 with Radio Frequency (RF) electrosurgical energy at different potentials to establish a potential gradient for conducting electrosurgical energy therebetween and through grasped tissue to electrosurgically treat, e.g., seal, tissue. Tissue contacting surfaces 114, 124 may alternatively be configured to supply or conduct any other suitable electrosurgical energy, e.g., microwave, light, ultrasonic, etc., to or through tissue grasped therebetween for electrosurgical tissue treatment. Tissue contacting surfaces 114, 124 may be defined on plates secured to jaw housings 112, 122, respectively, may be deposited onto jaw housings 112, 122, e.g., via sputtering or other suitable deposition technique, or may define any other suitable configuration. One or more stops (not shown) configured to inhibit shorting between tissue contacting surfaces 114, 124 may be disposed on either or both tissue contacting surfaces 114, 124.

Continuing with reference to FIGS. 4 and 5, one or both of the jaw members 110, 120, e.g., jaw member 120, includes a thermal cutting element 150 disposed therein and selectively deployable from a retracted position (FIG. 4), wherein thermal cutting element 150 is flush with or recessed within jaw member 120 (and does not protrude from tissue contacting surface 124), to an extended position (FIG. 5), wherein thermal cutting element 150 protrudes upwardly from tissue contacting surface 124 of jaw member 120, e.g., through channel 125 (FIGS. 1A and 1B) defined within tissue contacting surface 124 towards tissue contacting surface 114 of jaw member 110 (FIGS. 1A and 1B). In some configurations, tissue contacting surface 114 defines a channel (not shown, similar to channel 125 (FIGS. 1A and 1B)) for receipt of at least a portion of thermal cutting element 150 therein in the extended position of thermal cutting element 150 and the approximated position of jaw members 110, 120.

Thermal cutting element 150 defines an elongated configuration extending, in aspects, at least 85%, in other aspects at least 90%, and in still other aspects, at least 95% of the length of tissue contacting surface 124, although other configurations are also contemplated. In this manner, thermal cutting element 150 is capable of fully dividing sealed tissue grasped between tissue contacting surfaces 114, 124 regardless of the position of the sealed tissue or the length of sealed tissue. It is noted that, even though thermal cutting element 150 may not extend the entire length of tissue contacting surface 124, some tissue cutting may be enabled beyond the length of thermal cutting element 150, thus enabling tissue cutting the full length of tissue contacting surface 124. In other aspects, thermal cutting element 150 extends a smaller portion of the length of tissue contacting surface, the entire length of tissue contacting surface 124, or beyond the length of tissue contacting surface 124, e.g., to protrude distally therefrom to define a thermal probe to facilitate blunt dissection, spot cauterization or coagulation, enterotomies, etc. In any of the above-noted aspects, multiple thermal cutting elements 150 may be arranged lengthwise along jaw member 120 such that the thermal cutting elements 150 collectively define the desired length. In such aspects, the thermal cutting elements 150 may be independently deployable and/or activatable, or collectively deployable and/or activatable.

Thermal cutting element 150 may be formed from an electromagnetic material, e.g., a metal, and is configured to be inductively heated via a coil 156 disposed within outer jaw housing 122 of jaw member 120. In aspects, thermal cutting element 150 is formed from a ferromagnetic material.

Referring still to FIGS. 4 and 5, as noted above, a coil 156 is disposed within outer jaw housing 122 of jaw member 120. More specifically, coil 156 is an elongated electromagnetic induction coil 156 disposed within outer jaw housing 122 in fixed position therein (although, in some aspects, coil 156 may be movable with thermal cutting element 150 and relative to jaw member 120). Coil 156 is positioned to surround thermal cutting element 150 in a lengthwise direction and defines a height that extends at least a portion of a height of thermal cutting element 150, e.g., at least 40%, at least 50%, at least 60%, or any other suitable portion of the (or the entire) height of thermal cutting element 150. Coil 156 is configured to at least partially overlap with a height of thermal cutting element 150 in each of the retracted (FIG. 4) and extended (FIG. 5) positions. Coil 156 is further configured to electrically couple to generator "G" and, more specifically, a pair of electrical leads 157, 158 that are electrically isolated from one another are configured to connect to generator "G" and first and second end portions of coil 156 to enable energization of coil 156. When coil 156 is energized via energy from generator "G," coil 156 produces an electromagnetic field therein, which serves to inductively heat thermal cutting element 150.

The inductance and resistance of coil 156 are functions of the permeability of thermal cutting element 150. With respect to a ferromagnetic material(s) forming thermal cutting element 150, for example, permeability varies with temperature. From room temperature, for example, the permeability of a ferromagnetic material increases as temperature increases until reaching the Curie temperature, at which point the permeability decreases sharply to a substantially paramagnetic state. Thus, automatic, Curie-point temperature control may be implemented wherein thermal cutting element 150 is heated to and maintained at its Curie temperature by this variation in inductance or resistance as a function of temperature. Alternatively or additionally, this variation in inductance or resistance as a function of temperature can be used for temperature control at other temperatures and/or for temperature measurement (and control based thereon). That is, changes in inductance or resistance can be detected as changes in voltage, current, and/or phase angle between coil voltage and current, e.g., via generator "G", thus enabling temperature measurement. Feedback based voltage and/or current control (e.g., utilizing feedback as to voltage, current, and/or phase angle) can also be used to control heating and maintain thermal cutting element 150 at a target temperatures below its Curie point and/or to follow a heating temperature profile.

In aspects, control may be implemented by establishing an inductance-capacitance (LC) circuit from which oscillation frequency is derived. By providing a capacitor "C," e.g., within generator "G" or otherwise positioned, and with the inductance being the inductance of coil 156 and thermal cutting element 150, temperature can be determined based on the fact that the frequency of oscillation of the LC circuit is a function of temperature. Thus, at room temperature of thermal cutting element 150, for example, the LC circuit oscillates at a relatively low frequency. As coil 156 inductively heats thermal cutting element 150, the oscillation frequency decreases until thermal cutting element 150 reaches its Curie point temperature, at which time the oscillation frequency jumps to a relatively high frequency. The oscillation frequency of the LC circuit thus changes based upon the temperature of the thermal cutting element 150 and, thus, enables temperature control based on monitoring oscillation frequency. This variation in oscillation frequency as a function of temperature can be used to implement temperature control or temperature measurement, similarly as detailed above with respect to inductance variation as a function of temperature.

In aspects, the heating of thermal cutting element 150 and the deployment of thermal cutting element 150 may be independent of one another; in other aspects, the heating of thermal cutting element 150 and the deployment of thermal cutting element 150 may be coupled to one another. For example: deployment of thermal cutting element 150 to the extended position may initiate heating of thermal cutting element 150 (at the beginning of deployment, after completion of deployment, or at any other position therebetween), e.g., as detailed above with respect to switch 6 and trigger 62 (FIGS. 1A and 1B); return of thermal cutting element 150 to the retracted position may deactivate heating of thermal cutting element 150 (at the beginning of return, after completion of return, or at any other position therebetween) e.g., likewise utilizing switch 6 and trigger 62 (FIGS. 1A and 1B); heating of thermal cutting element 150 may be inhibited until thermal cutting element 150 is deployed to the extended position; heating of thermal cutting element 150 may be inhibited when thermal cutting element 150 is not disposed in the extended position; deployment of thermal cutting element 150 to the extended position may be inhibited until thermal cutting element 150 is sufficiently heated (e.g., to its Curie temperature, other temperature set-point, a minimum temperature threshold, etc.); return of thermal cutting element 150 to the retracted position may be inhibited until thermal cutting element 150 is sufficiently cooled; etc.

Thermal cutting element 150, in the extended position (FIG. 5), and/or while moving to the extended position (FIG. 5), may be utilized to statically and/or dynamically thermally treat, e.g., cut, tissue grasped between jaw members 110, 120 (for example, after sealing tissue); may be utilized to statically and/or dynamically thermally treat tissue in a jaws open condition, e.g., via tenting; and/or may be utilized in any other suitable matter to facilitate static and/or dynamic thermal tissue treatment.

Turning to FIGS. 6-9, various deployment mechanisms for selectively deploying thermal cutting element 150 from the retracted position (FIG. 4) to the extended position (FIG. 5) are provided. In aspects, the deployment mechanisms detailed below with respect to FIGS. 6-9 may be operably coupled to trigger assembly 60 (FIGS. 1A and 1B) such that actuation of trigger 62 (FIGS. 1A and 1B) induces the requisite motion to actuate the deployment mechanism to deploy thermal cutting element 150 from the retracted position (FIG. 4) to the extended position (FIG. 5) and/or return thermal cutting element 150 from the extended position (FIG. 5) to the retracted position (FIG. 4). Further, the deployment mechanisms detailed below with respect to FIGS. 6-9 may be utilized in conjunction with any of the above-detailed control features and/or interdependencies between the heating of thermal cutting element 150 and the deployment of thermal cutting element 150.

Figure 6:
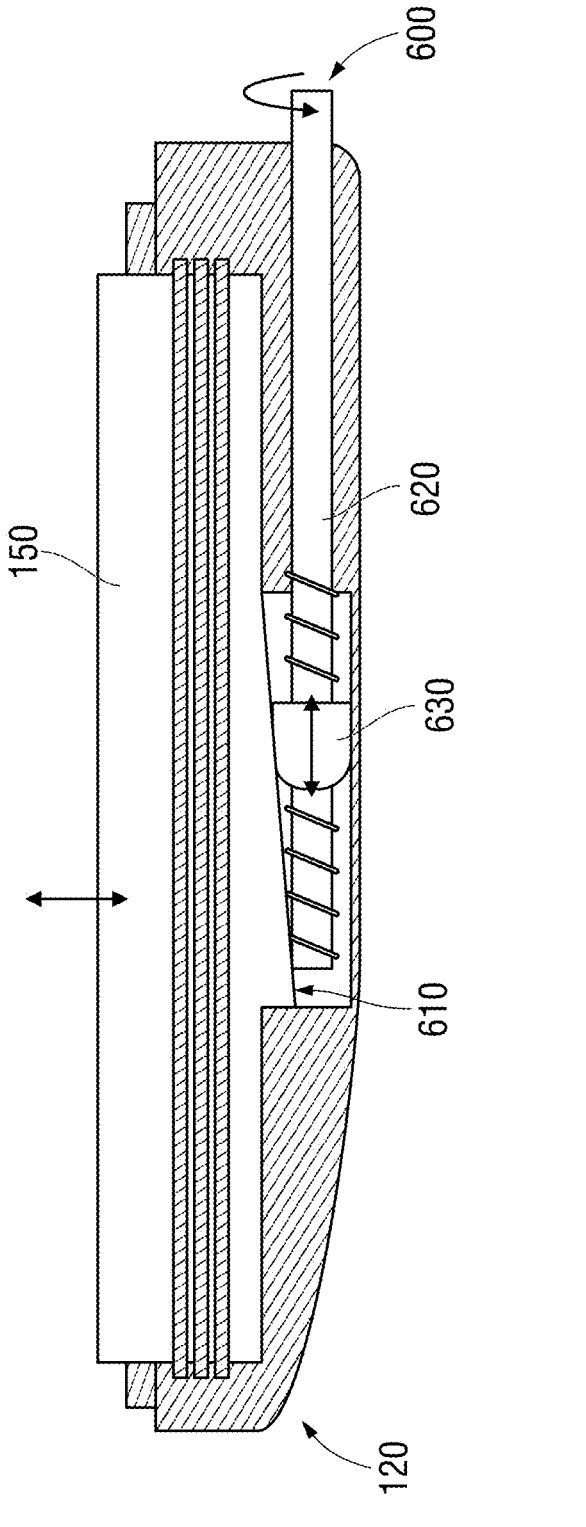
FIGS. 6-9 are longitudinal, cross-sectional views of a jaw member of the end effector assembly of FIG. 4 including various deployment mechanisms for selectively deploying the thermal cutting element to the extended position.

Referring to FIG. 6, a deployment mechanism 600 disposed within jaw member 120 is shown generally including an angled cam surface 610 attached to or formed with thermal cutting element 150, a threaded shaft 620, and a cam block 630 threadingly engaged about threaded shaft 620. Threaded shaft 620 may extend proximally from jaw member 120 through shaft 12 and into housing 20 to operably couple with trigger assembly 60 (see FIGS. 1A and 1B), or suitable connecting structures extending through shaft 12 and into housing 20 may be provided to operably couple threaded shaft 620 with trigger assembly 60 (see FIGS. 1A and 1B) such that actuation of trigger 62 (see FIGS. 1A and 1B) drives rotation of threaded shaft 620.

Cam block 630, as noted above, is threadingly engaged about threaded shaft 620. As such, rotation of threaded shaft 620 in a first rotational direction, e.g., counterclockwise, translates cam block 630 along threaded shaft in a first longitudinal direction, e.g., distally. On the other hand, rotation of threaded shaft 620 in a second, opposite rotational direction, e.g., clockwise, translates cam block 630 along threaded shaft in a second, opposite longitudinal direction, e.g., proximally. Cam block 630, in turn, is positioned to interact with angled cam surface 610 upon translation of cam block 630 and, more specifically, such that, upon translation of cam block 630 in the first longitudinal direction, cam block 630 urges angled cam surface 610 and, thus, thermal cutting element 150 from the retracted position towards the extended position and such that, upon translation of cam block 630 in the second, opposite longitudinal direction, cam block 630 is displaced from angled cam surface 610 and, thus, thermal cutting element 150 is permitted to return from the extended position back towards the retracted position. In aspects, thermal cutting element 150 is biased towards the retracted position, e.g., via one or more coil springs (see FIG. 10), flat springs (see FIG. 11), or in any other suitable manner, to facilitate the return thereof.

Figure 7:
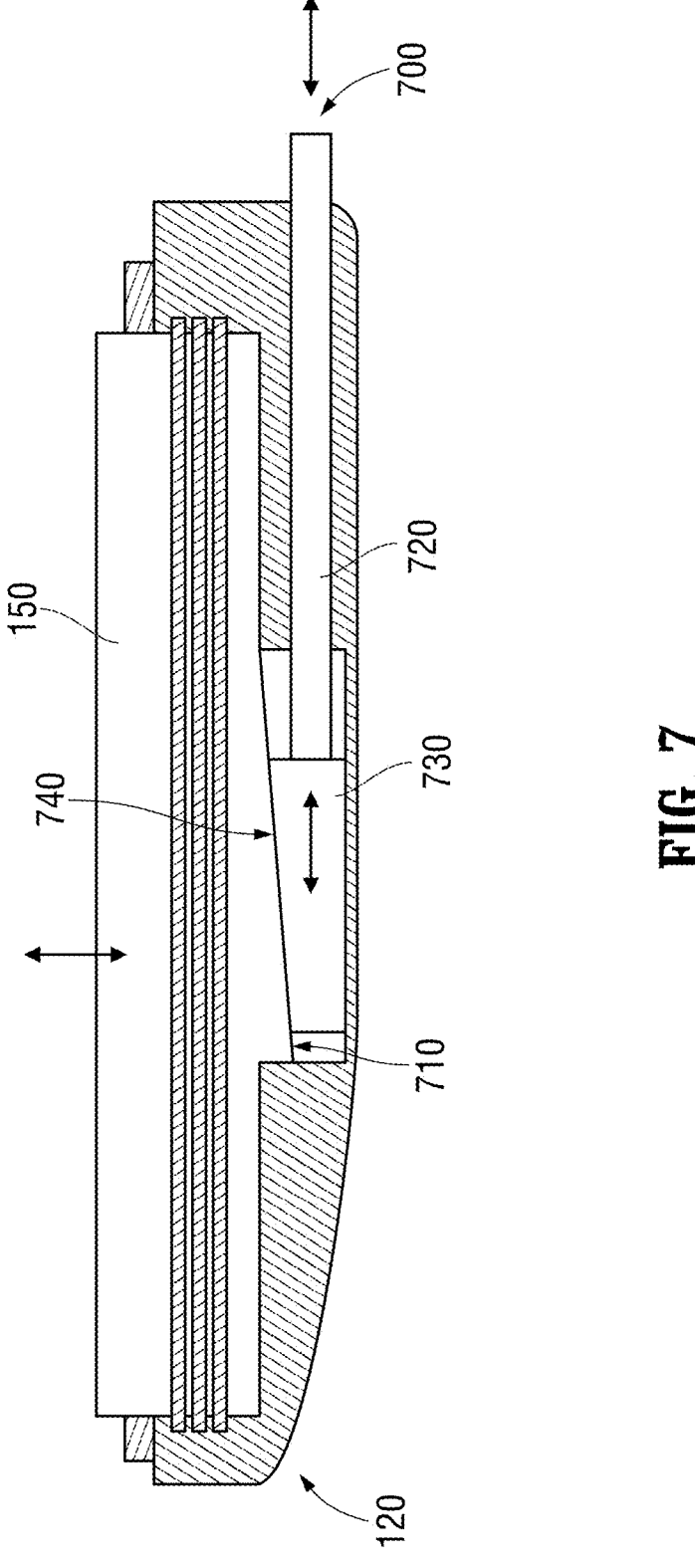

With reference to FIG. 7, another deployment mechanism 700 disposed within jaw member 120 is shown generally including an angled cam surface 710 attached to or formed with thermal cutting element 150, a drive shaft 720, and a cam block 730 fixedly engaged with drive shaft 720 and defining an oppositely angled cam surface 740 as compared to cam surface 710. Drive shaft 720 may extend proximally from jaw member 120 through shaft 12 and into housing 20 to operably couple with trigger assembly 60 (see FIGS. 1A and 1B), or suitable connecting structures extending through shaft 12 and into housing 20 may be provided to operably couple drive shaft 720 with trigger assembly 60 (see FIGS. 1A and 1B) such that actuation of trigger 62 (see FIGS. 1A and 1B) translates drive shaft 720.

As a result of the above-detailed configuration, translation of drive shaft 720 in a first direction, e.g., distally, translates cam block 730 in a similar direction such that cam surface 740 of cam block 730 interacts with angled cam surface 710 to urge angled cam surface 710 and, thus, thermal cutting element 150 from the retracted position towards the extended position, and such that translation of drive shaft 720 in a second, opposite direction, e.g., proximally, translates cam block 730 in a similar direction such that cam surface 740 is displaced from angled cam surface 710 and, thus, thermal cutting element 150 is permitted to return from the extended position back towards the retracted position. In aspects, thermal cutting element 150 is biased towards the retracted position, e.g., via one or more coil springs (see FIG. 10), flat springs (see FIG. 11), or in any other suitable manner, to facilitate the return thereof.

Figure 8:
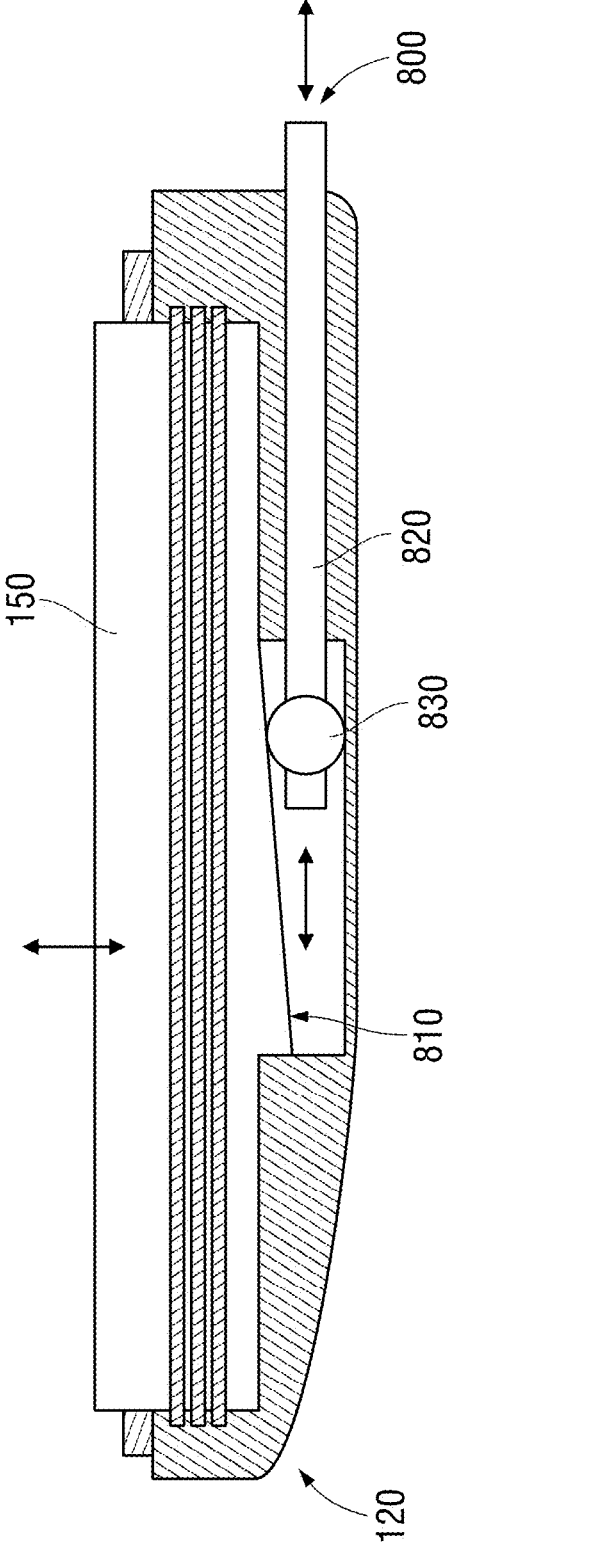

Still another deployment mechanism 800 disposed within jaw member 120 is illustrated in FIG. 8. Deployment mechanism 800 includes an angled cam surface 810 attached to or formed with thermal cutting element 150, a drive shaft 820, and a cam roller 830 rotatably mounted on drive shaft 820. Deployment mechanism 800 is similar to deployment mechanism 700 (FIG. 7) except that, rather than cam surface 740 of cam block 730 interacting with cam surface 710 upon translation of drive shaft 720 (see FIG. 7), cam roller 830 is configured to interact with, and roll along, cam surface 810 upon translation of the drive shaft 820.

Figure 9:
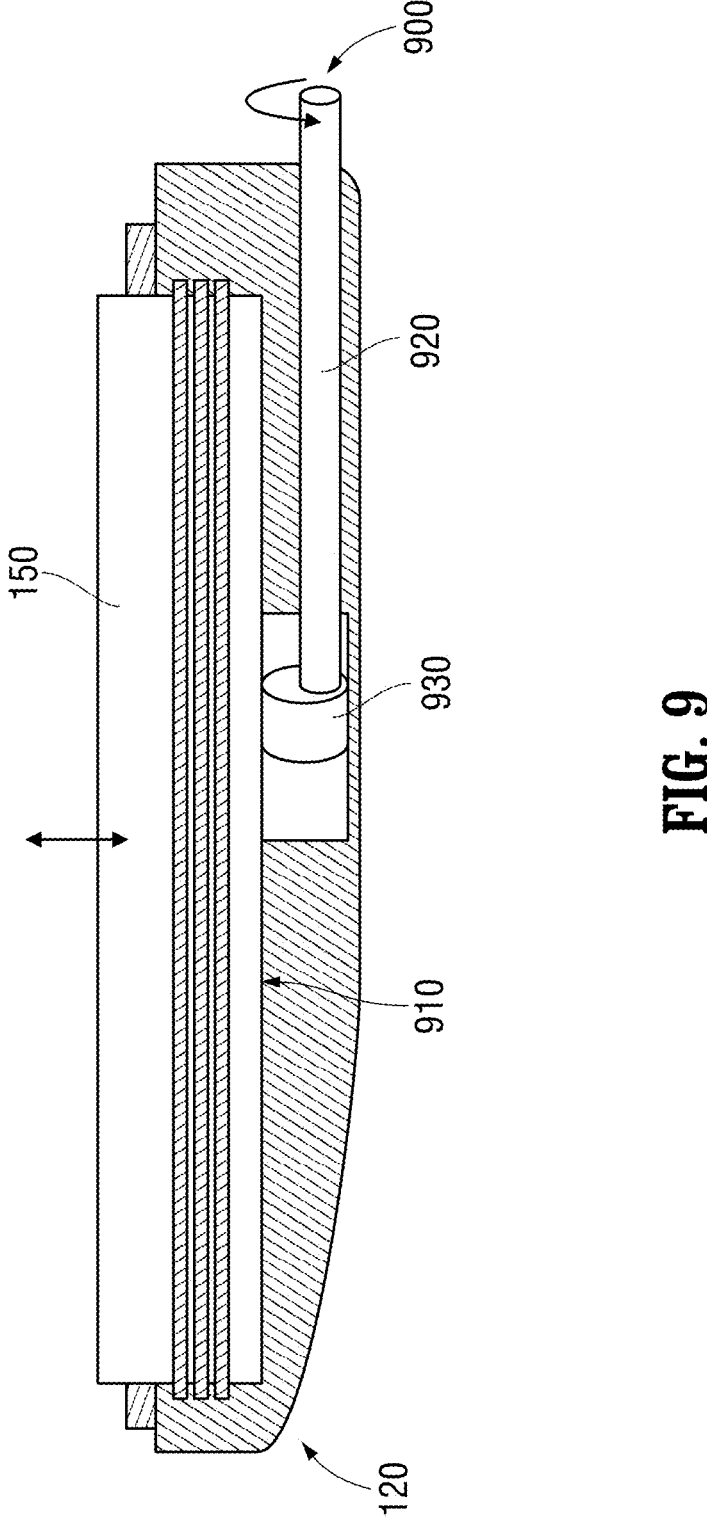

FIG. 9 illustrates yet another a deployment mechanism 900 disposed within jaw member 120. Deployment mechanism 900 includes a contact surface 910 attached to or formed with thermal cutting element 150, a rotatable drive shaft 920 disposed within jaw member 120, and a cam lobe 930 engaged with drive shaft 920 in an off-center position relative to a longitudinal axis of rotatable drive shaft 920 such that, in a first orientation of rotatable drive shaft 920, cam lobe 930 is urged into contact with contact surface 910 to thereby urge thermal cutting element 150 from the retracted position towards the extended position and such that, in a second orientation of rotatable drive shaft 920, cam lobe 930 is displaced from contact surface 910 to allow thermal cutting element 150 to return from the extended position back towards the retracted position. In aspects, thermal cutting element 150 is biased towards the retracted position, e.g., via one or more coil springs (see FIG. 10), flat springs (see FIG. 11), or in any other suitable manner, to facilitate the return thereof.

Figure 10:
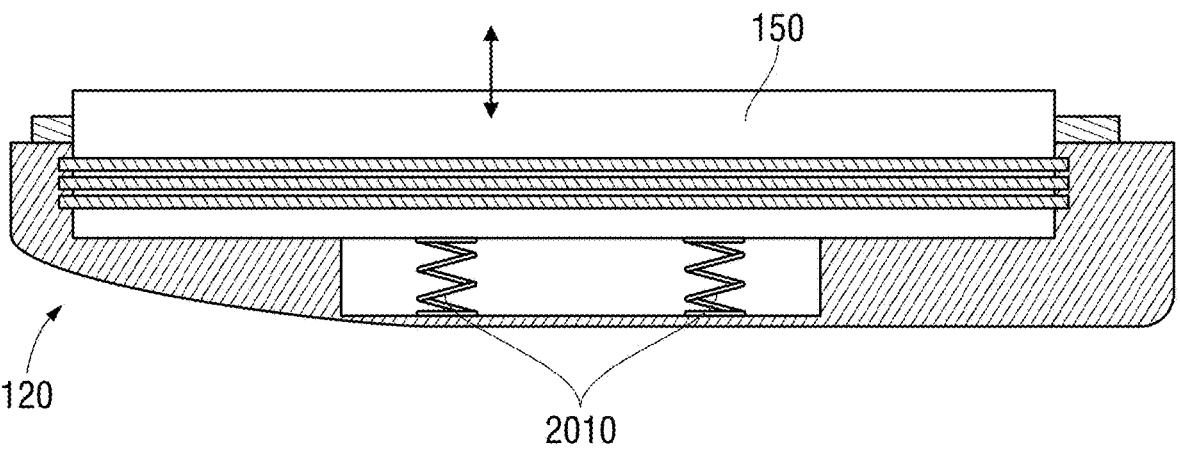
FIGS. 10 and 11 are longitudinal, cross-sectional views of the jaw member of FIG. 4 including biasing mechanisms for biasing the thermal cutting element.
Figure 11:
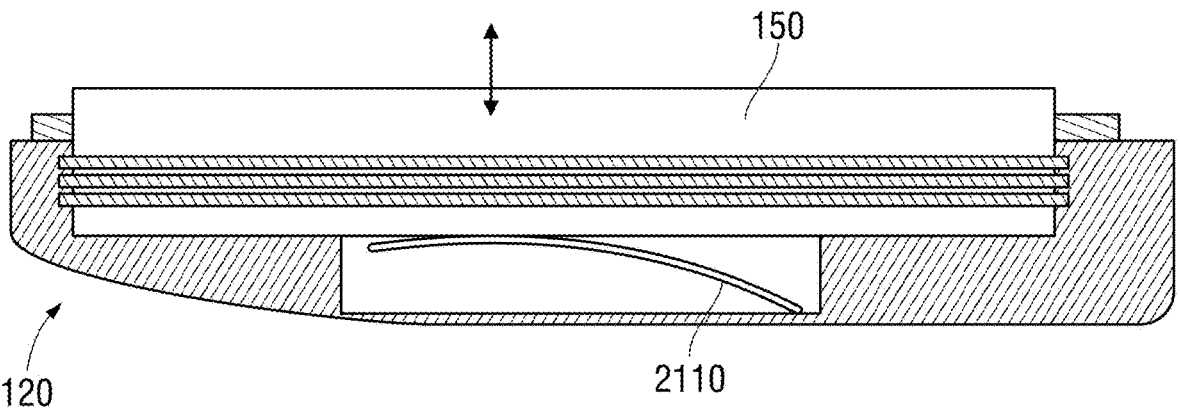

Referring to FIGS. 10 and 11, alone or in combination with any of the deployment mechanisms detailed herein (see FIGS. 6-9) or any other suitable deployment mechanism, a biasing mechanism may be disposed within jaw member 120 (and/or jaw member 110 if jaw member 110 additionally or alternatively incorporates a thermal cutting element) to bias thermal cutting element 150. More specifically, with reference to FIG. 10, one or more coil springs 2010 may be disposed within jaw member 120 and configured to act on thermal cutting element 150 (directly or indirectly) to bias thermal cutting element 150 towards the extended position. Alternatively, the one or more coil springs 2010 may be configured to act on thermal cutting element 150 (directly or indirectly) to bias thermal cutting element 150 towards the retracted position and any of the deployment mechanisms detailed herein (see FIGS. 6-9), or any other suitable deployment mechanism may be utilized to deploy thermal cutting element 150 against this bias. Turning to FIG. 11, the one or more flat springs 2110 disposed within jaw member 120 and configured to act on thermal cutting element 150 (directly or indirectly) may likewise be utilized to bias thermal cutting element 150 towards the extended position or the retracted position.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:
1. A surgical system, comprising:
an end effector assembly, including:
first and second jaw members each including a tissue contacting surface, at least one of the first or second jaw members movable relative to the other between a spaced apart position and an approximated position for grasping tissue between the tissue contacting surfaces;

an electromagnetic induction coil disposed within the second jaw member; and a thermal cutting element disposed at least partially within the electromagnetic induction coil and movable relative to the electromagnetic induction coil and the second jaw member between a retracted position and an extended position different from the retracted position, wherein the thermal cutting element protrudes from the second jaw member in the extended position, wherein the thermal cutting element is formed at least partially from an electromagnetic material capable of being inductively heated, and wherein the electromagnetic induction coil is adapted to connect to a source of energy to produce an electromagnetic field within the electromagnetic induction coil to thereby inductively heat the thermal cutting element.

2. The surgical system according to claim 1, wherein the tissue contacting surfaces are formed from an electrically-conductive material and adapted to connect to a source of energy for electrosurgically treating tissue grasped between the tissue contacting surfaces.

3. The surgical system according to claim 1, wherein the tissue contacting surface of the second jaw member defines a channel therethrough and wherein, in the extended position, the thermal cutting element protrudes through the channel to extend from the tissue contacting surface of the second jaw member.

4. The surgical system according to claim 1, wherein the thermal cutting element is biased towards the retracted position or the extended position.

5. The surgical system according to claim 1, further comprising a deployment mechanism for selectively moving the thermal cutting element from the retracted position to the extended position.

6. The surgical system according to claim 5, wherein the deployment mechanism includes a threaded drive shaft including a cam block threadingly engaged thereon, and wherein rotation of the threaded drive shaft translates the cam block to interact with a cam surface associated with the thermal cutting element to move the thermal cutting element towards the extended position.

7. The surgical system according to claim 5, wherein the deployment mechanism includes a drive shaft including a cam block engaged therewith, and wherein translation of the drive shaft translates the cam block to interact with a cam surface associated with the thermal cutting element to move the thermal cutting element towards the extended position.

8. The surgical system according to claim 5, wherein the deployment mechanism includes a drive shaft including a cam roller rotatably engaged therewith, and wherein translation of the drive shaft translates the cam roller to roll along a cam surface associated with the thermal cutting element to move the thermal cutting element towards the extended position.

9. The surgical system according to claim 5, wherein the deployment mechanism includes a drive shaft having a cam lobe engaged therewith in an offset position, and wherein rotation of the drive shaft rotates the cam lobe to interact with a cam surface associated with the thermal cutting element to move the thermal cutting element towards the extended position.

10. The surgical system according to claim 1, wherein deployment of the thermal cutting element and heating of the thermal cutting element are independently initiated.

11. The surgical system according to claim 1, wherein deployment of the thermal cutting element and heating of the thermal cutting element are at least partly dependent upon one another.

12. The surgical system according to claim 11, wherein one of deployment or retraction of the thermal cutting element is inhibited based on a temperature of the thermal cutting element.

13. The surgical system according to claim 11, wherein heating of the thermal cutting element is inhibited based on a position of the thermal cutting element.

14. The surgical system according to claim 1, wherein the thermal cutting element is formed at least partially from a ferromagnetic material.

15. The surgical system according to claim 14, wherein a temperature of the thermal cutting element controlled based upon a Curie point temperature of the thermal cutting element via automatic Curie point temperature control.

16. The surgical system according to claim 14, further comprising an LC circuit configured to enable temperature-based control of heating of the thermal cutting element based on a relationship between oscillation frequency of the LC circuit and temperature of the thermal cutting element.

17. The surgical system according to claim 14, further comprising a generator configured to monitor inductance or resistance of the thermal cutting element and to enable temperature-based control of heating of the thermal cutting element based on a relationship between inductance or resistance of the thermal cutting element and temperature of the thermal cutting element.

* * * * *